United States Patent [19]

Holbrook et al.

[11] 3,960,165
[45] June 1, 1976

[54] FLUID COLLECTION BOTTLE WITH IMPROVED AIR FLOW VALVE MEANS

[75] Inventors: Legrand K. Holbrook, Salt Lake City; Gary F. Sturdevant, Sandy, both of Utah

[73] Assignee: Medical Development Corporation, Salt Lake City, Utah

[22] Filed: Nov. 7, 1974

[21] Appl. No.: 521,560

Related U.S. Application Data

[63] Continuation-in-part of Ser. No. 407,298, Oct. 17, 1974, abandoned.

[52] U.S. Cl.............................. 137/202; 137/205; 137/433; 128/276
[51] Int. Cl.².................. A61M 1/00; F16K 31/22
[58] Field of Search................... 137/202, 205, 433; 128/276

[56] References Cited
UNITED STATES PATENTS

| | | | |
|---|---|---|---|
| 2,949,926 | 8/1960 | Hanin | 137/202 |
| 3,401,751 | 9/1968 | Loftin | 137/202 X |

FOREIGN PATENTS OR APPLICATIONS

| | | | |
|---|---|---|---|
| 1,185,880 | 1/1965 | Germany | 137/202 |

*Primary Examiner*—Alan Cohan
*Attorney, Agent, or Firm*—Fitch, Even, Tabin & Luedeka

[57] ABSTRACT

A vacuum operated fluid collection bottle including a fluid inlet port and also a vacuum port, with the vacuum port being provided with an improved vacuum shut-off valve provided with an air deflecting baffle. Such baffle is disposed underneath the valve element or valve gate and is spaced therefrom. The purpose for the baffle is to deflect air essentially around the valve gate so that the pressure of onrushing air, due to the imposition of a vacuum condition, will not cause the valve gate to close prematurely. Thus, the valve gate, even though made of lightweight material, will be permitted simply to float upwardly in response to the rise of fluid level within the bottle until an essentially bottle-filled condition is reached, at which point the lightness of the valve gate will be responsive to the reduced pressure area at the vacuum port so as to suck into and tightly seat against the valve seat provided therefor.

1 Claim, 5 Drawing Figures

U.S. Patent June 1, 1976 3,960,165
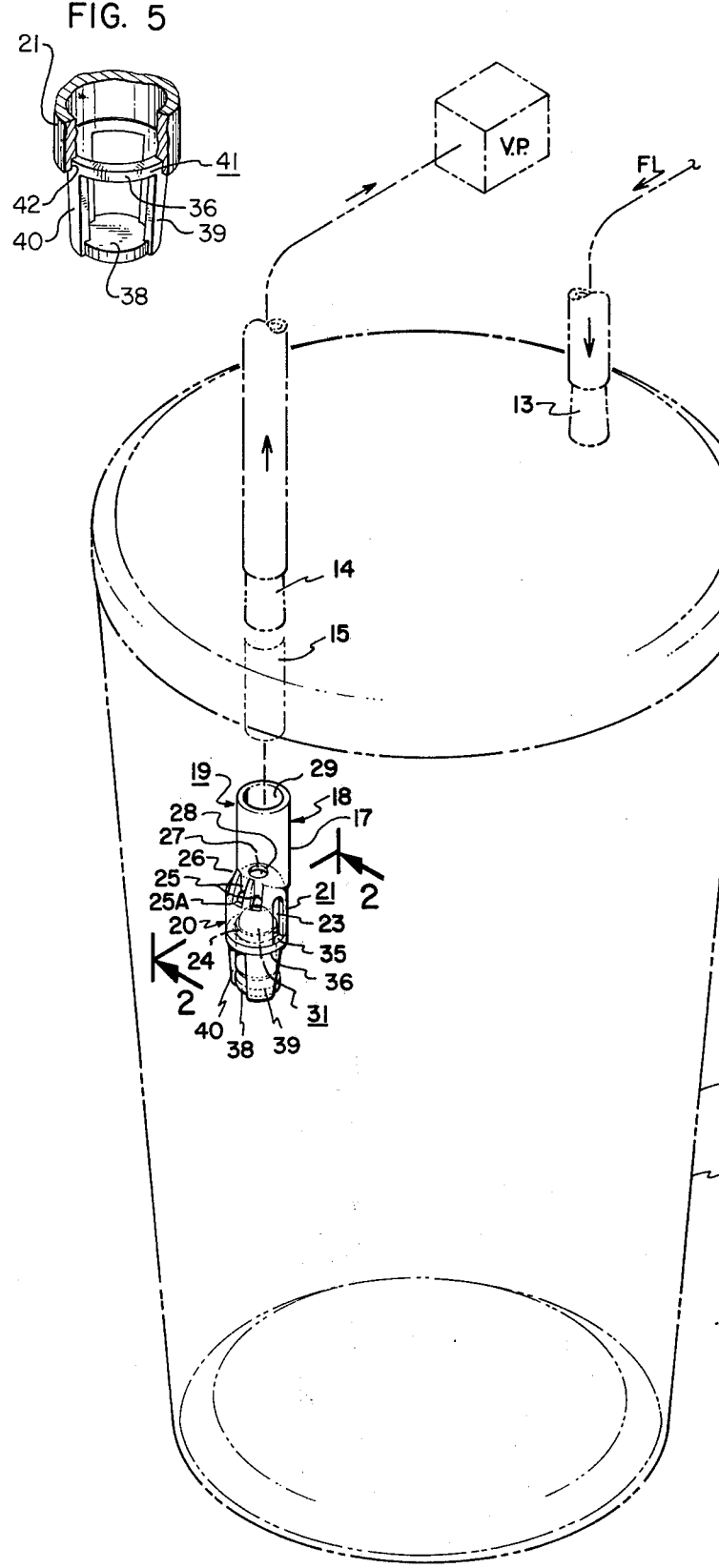
FIG. 1
FIG. 5
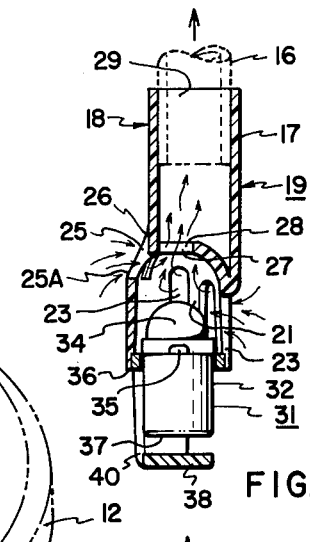
FIG. 2
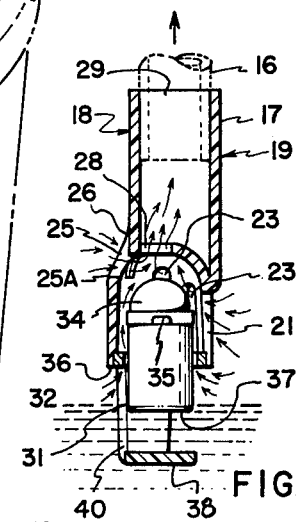
FIG. 3
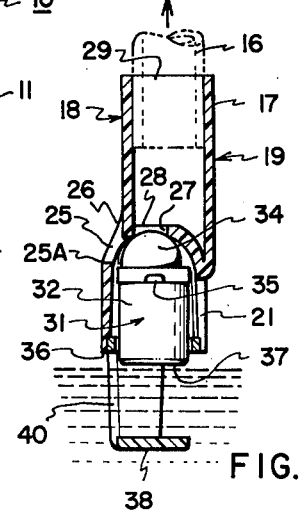
FIG. 4

FLUID COLLECTION BOTTLE WITH IMPROVED AIR FLOW VALVE MEANS

This is a continuation-in-part of the inventor's prior patent application entitled FLUID COLLECTION BOTTLE WITH IMPROVED AIR FLOW VALVE MEANS, Ser. No. 407,298, filed Oct. 17, 1973 now abandoned.

The present invention relates to vacuum operated fluid collection bottles such as aspiration bottles used in hospital surgical stations and recovery rooms and, more particularly, to a new and improved fluid collection bottle containing an improved valve employed at the vacuum port of the bottle.

The present invention represents an improvement in the bottle and valve as related to the inventor's copending application entitled, Valve and Related Structure for Vacuum operated Liquid-filled Bottles, Ser. No. 250,982, filed May 8, 1972 (Group 44), now U.S. Pat. No. 3,811,485.

Several criteria require consideration in suitably discerning a vacuum operated liquid fill bottle incorporating a valve at the vacuum port of the bottle. As is described in the inventor's copending application that is referenced, the valve is used as a direct float valve responsive to the rising fluid level within the bottle, and operates to shut off or close the vacuum port, in response to a pre-determined rise in the fluid level, this so that the bottle will not be further filled, fluid will not enter the vacuum system, and so forth.

In order to keep bone fragments, mucous, tissue, and forth away from the valve seat, it is necessary that the valve gate be as lightweight as possible. The inventor has found to date that, notwithstanding the lightness of the material employed for fabricating the valve gate, the same still should be made hollow interiorly so the base of the valve gate will rise as close to the surface of the rising fluid level as possible. But the necessary lightness in the valve raises another problem, namely, that of pre-closing the valve, minus baffle, immediately upon the imposition of a vacuum pressure on the order of from 15 to 20 inches of mercury. Thus, the vacuum applied causes an immediate onrush of air within the bottle, upwardly against the bottom of the float, serving to preliminarily close the float valve even before any fluid is entered the bottle. It has been discovered that there may be advantageously placed an air-deflecting baffle beneath the float valve so that this pre-closing phenomenon is avoided. Accordingly, air within the bottle beneath the float valve is deflected away from the base thereof so that the float valve remains in its intended lower condition, awaiting arrival of the surface of the fluid level to which will gradually rise within the bottle. In the absence of a baffle, then there is great danger, particularly when operating at high vacuum pressures, for the valve to close prematurely and immediately upon the application of a vacuum, this through the sucking action generated and the consequent onrush upwardly of air within the bottle beneath and there impinging on the float.

In the present invention the baffle is suspended beneath the float by the former's inclusion in a baffle support member that is secured to the valve body portion surrounding the float.

Accordingly, an object of the present invention is to provide a new and improved vacuum operated liquid fill bottle incorporating novel valve means proximate the vacuum port thereof.

A further object of the invention is to provide a valve having an air deflecting baffle spacedly disposed beneath the valve gate of such valve.

A further object is to provide a lightweight valve construction in a vacuum-operated liquid fill bottle wherein, by the design of such valve, the same will be precluded from closing upon the initial application of vacuum to the vacuum port of such bottle.

An additional object is to provide an improved valve construction having a lightweight valve gate provided with an air deflector disposed underneath the same to preclude inadvertent, premature valve closing.

The features of the present invention may best be understood by reference to the following description taken in connection with the accompanying drawing in which:

FIG. 1 is a side elevation of a vacuum operated liquid fill bottle incorporating the subject baffle provided valve; for convenience of illustration of valve is exploded downwardly from the vacuum port to which the same is connected.

FIG. 2 is an enlarged, section detail taken along the line 2—2 in FIG. 1, indicating the disposition of the valve prior to and at imposition at negative pressure at the vacuum port.

FIG. 3 is similar to FIG. 2 but illustrates the gradually rising valve gate in response to the upward pressure of the rising fluid level surface of fluid being aspirated into the bottle.

FIG. 4 is similar to FIG. 3 but illustrates valve closure in response to the further rising of the fluid level to carry the valve gate proximate its seat; at approximately such position the suction provided will completely urge the gate against its seat and raise the base of the valve gate slightly above the now stationary fluid level.

FIG. 5 is a fragmentary enlarged perspective view of the baffle and support structure as contemplated in the invention.

In the drawings the vacuum operated liquid-fill bottle 10 is shown in phantom lines and its particular design. The vacuum bottle 10 will include the usual container 11 and lid 12, these to be fitted thereover. Lid 12 will be provided with fluid inlet port 13 and vacuum port 14. A vacuum pump V.P. and its conduit will be coupled to and hence communicate with vacuum port 14. The lower extremity 15 of vacuum port 14 will be tapered slightly at 16 to receive in a press or wedging fit tubular mount 17 of the subject valve 18. Tubular mount or upper mounting portion 17, in fact, forms a part of valve housing 19, and the latter includes, depending from tubular mount 17, a valve body portion 20 which is offset from tubular mount 17. Such offset reduces valve length and accommodates close proximity of the vacuum port with the container lid edge.

The valve body portion or guide structure 20 includes a valve cage 21 provided with upstanding bar portions 22 defining open spaces 23. A slit portion or shield 24 extends partially around the transverse periphery of valve body portion 20 as indicated. Most importantly, air vents or vent openings 25 are provided above shield 24. Valve body or lower valve guide portion 20 and tubular mount 17 meet in a common juncture 26 at which an upwardly tapered valve seat 27 is provided annularly about communicative opening 28. Communicative opening 28, of course, provides communication as between the interior elongate aperture 29 of tubular mount 17 and the interior 30 of the valve body portion 21. Valve member 31 itself includes a hollow valve cup 32, as shown and fitted into upper extremity 33 of the latter is an essentially cone-shaped valve element 34. Valve element 34 is designed to seat against the valve seat 27. Valve cup 32 is preferably made of polystyrene so as to be lightweight and hence preserve the float valve characteristics of valve member 31. Ears or tabs 35 are provided the valve 31, and these ears operate as stops for engagement with the ring shaped base portion 36 of valve body portion 20. It is noted that the tubular mount 17 is offset relative to the vertical axis of the valve body portion 20. This is also for the purpose of providing a peripheral region as at 25A so that the air vents 25 can be provided.

The subject valve is especially suitable for use in the design of body fluid aspiration bottles for hospital use. Where the aspiration bottle 10, for example, incorporates the subject valve of the present invention, then the same is provided an automatic, fluid-level controlled float valve to automatically shut off or isolate the negative pressure source, i.e., a vacuum pump, from direct communication with the interior of the aspiration or liquid-fill bottle 10, and hence termiante fluid flow. Thus, the vacuum supply being cut off from the bottle, additional fluid as from the patient's operative area will not continue to pour in through fluid inlet port 13.

Valve member 31 is ideally seated as a float and is kept from dropping out of the valve housing by virtue of ears 35 and their abutment engagement with ring shaped base portion 36.

For many types of surgery much solid material such as tissue and bone fragments may be found in the incoming body fluid or blood stream coming into the bottle via fluid inlet port 13. Shield 24 operates to prevent such bone and tissue fragments from clogging the valve. Yet, it has been found through experimentation that air vents about the valve must be supplied both above the shield, as at 25, and also about the opposite side of the valve area proximate openings 23. If either of the sets of openings 25 or 23 are eliminated, then negative or vacuum pressure as supplied tubular mount 17 via the operating vacuum pump (not shown) will itself operate to close the valve, i.e., to draw valve 31 upwardly to close against valve seat 27. It is desirous to mold the valves as lightweight as possible and to use as little material as possible. Polyethylene plastic ideally serves as a material for use here. But when such is the case, a maximum air-flow is needed completely above the valve element 34 prior to its ascent to its valve seat. Accordingly, air vents must be supplied both above the shield 24 and also on the opposite side as at 23. Such a peripheral vent pattern will insure that valve ascent enclosure will be dependent solely upon rising fluid level and the engagement thereof with base 37 of the valve member 31. Thus, shield 24 keeps bone fragments and tissue from clogging the valve, and the air vents above the shield 24, as at 25, with air vents or openings 23 serve to provide for a maximum air-flow across the valve, thus precluding inadvertent raising of the valve solely upon the application of vacuum pressure. It is known that by virtue of the above design the lower peripheral air vents at 23 may be oriented close to the inside wall of the bottle so as to further tend to eliminate possibilities of clogging the valve by solid material contained within the body fluid.

Most important in the invention is the inclusion of air deflecting baffle 38. The baffle is preferably designed to approximate in area the transverse cross-section of valve member 31. The latter is supported underneath the base 37 of the valve member 31. Specifically, baffle support member 41 includes an upper portion, e.g. a ring portion 36 and depending arms 39 and 40 which depend therefrom. The latter may be recessed at their lower edges to receive the baffle 38 that can be cemented or simply pressed in place. Alternatively, the baffle 38 may be integrally formed with the depending arms 39 and 40, along with ring portion 36. Valve body 21 includes an inner annular recessed seat 42 which receives ring portion 36 at a cemented or simply press-fit juncture. FIG. 5 is herein given in further explanation of the structure as shown in FIGS. 3 and 4.

Where desired, the valve body structure may be modified so as not to include shield 24, but where sufficient openings as at 25 are still included to provide the air passage above explained and as shown in FIG. 2.

Accordingly, upon the initial application of vacuum by vacuum pump V.P., the air will tend to be evacuated from or sucked out of the interior of bottle 10 via vacuum port 14 and the line connected thereto leading to the vacuum pump. The onrush of air upwardly will now not impinge directly upon base 37 of valve member 31 but rather will proceed along the side thereof and enter the valve body as shown by the several arrows in FIG. 3. In this manner there is no possibility of a premature closing of the valve due to an immediately imposition of suction or negative pressure at vacuum port 14. Rather, and owing to the air passage as illustrated in FIG. 3, the valve or valve gate 31 will simply remain in its rest position as shown in FIGS. 1 and 2 until the fluid level within the bottle gradually rises to the point indicated in FIG. 3, namely at a point proximate base 37 of valve member 31. At this point it is the fluid level that causes the valve member 31 to rise. The rising fluid level as further seen in FIG. 4 raises the valve member near its seat, at which point the suction within port 14 serves immediately to close the valve and hence remove the vacuum pressure source effectively from the interior of the bottle so as to stop fluid-flow within float inlet port 13.

While particular embodiments of the invention have been shown and described, it will be obvious to those skilled in the art the various changes and modifcations which may be made without departing from the essential features of the present invention and, therefore, the aim in the appended claims is to cover all such changes and modifications as fall within the true spirit and scope of the invention.

We claim:

1. An air-passage closure float valve device including, in combination, an elongate float valve; guide structure housing said float valve for vertical movement of the latter, said float valve and said guide structure having mutually inter cooperable means for enabling and also limiting the downward protrusion of said float valve beneath said guide structure; and a baffle support member having an upper portion secured to said structure, a baffle, and means depending from said upper portion for supporting said baffle in spaced relationship beneath said float valve for all dispositions of the latter, and wherein said guide structure is provided with a downwardly facing recessed seat, said upper portion comprising a ring being secured in said recessed seat.

* * * * *